United States Patent [19]
Diamond et al.

[11] Patent Number: 5,567,596
[45] Date of Patent: Oct. 22, 1996

[54] RAPID ASSAY OF ACTIVATORS AND INHIBITORS OF CLOTTING

[75] Inventors: Scott L. Diamond, Snyder; Jung-He Wu, Amherst, both of N.Y.

[73] Assignee: Research Foundation of State University of New York, Amherst, N.Y.

[21] Appl. No.: 365,780

[22] Filed: Dec. 29, 1994

[51] Int. Cl.$^6$ .................................................. C12Q 1/56
[52] U.S. Cl. ............................ 435/13; 435/4; 435/23; 435/24; 435/968; 436/536; 436/546; 436/69; 436/800
[58] Field of Search ..................... 435/4, 13, 23, 435/24, 968; 436/536, 546, 69, 800

[56] References Cited

U.S. PATENT DOCUMENTS

| | | | |
|---|---|---|---|
| 4,046,635 | 9/1977 | Moroz | 435/13 |
| 4,668,621 | 5/1987 | Doellgast | 435/13 |
| 4,668,623 | 5/1987 | Kinnunen et al. | 435/19 |
| 5,071,745 | 12/1991 | Triscott et al. | 435/13 |
| 5,188,940 | 2/1993 | Krause et al. | 435/13 |
| 5,223,437 | 6/1993 | Hoffman et al. | 435/13 X |
| 5,344,783 | 9/1994 | Scarborough et al. | 436/69 X |
| 5,350,676 | 9/1994 | Oberhardt et al. | 435/13 |

OTHER PUBLICATIONS

F. S. Stevens, "Polymeric Collagen Fibrils: An Example of Substrate–Mediated Steric Obstruction of Enzymic Digestion," Biochimica et Biophysica Acta, 452 (1976): 151–160.
D. Smith et al., "A Sensitive and Specefic Assay for Plasminogen Activators," Thrombosis Research, 37(1985): 533–541.

*Primary Examiner*—Carol A. Spiegel
*Attorney, Agent, or Firm*—Hodgson, Russ, Andrews, Woods & Goodyear

[57] ABSTRACT

Assays and reagents are provided for the measurement of components that are involved in either enzyme-catalyzed degradation of a substrate, such as in fibrinogenolysis or fibrinolysis; or enzyme-catalyzed polymerization of a substrate, such as in fibrinogen polymerization into fibrin. The method involves using a fluorescent-labeled substrate in an enzyme-catalyzed reaction, and measurement of the component's effects on the fluorescence emission of the enzyme-catalyzed reaction such as quenching or dequenching, as a measure of the component's activity.

26 Claims, 11 Drawing Sheets

RAPID ASSAY OF ACTIVATORS AND INHIBITORS OF CLOTTING

This invention was made, in part, with support from the American Heart Association. The American Heart Association has certain rights in this invention.

FIELD OF THE INVENTION

The present invention relates to rapid and sensitive fluorescence assays and assay reagents for measuring body fluid components involved in protein polymer formation and protein polymer degradation. More particularly, the invention discloses assays and assay reagents for the activity of blood components which are involved or active in clot formation, such as in fibrinogen polymerization; and for the activity of components which are involved or active in clot degradation such as in fibrinogenolysis, or fibrinolysis.

BACKGROUND OF THE INVENTION

In the field of biomedicine, there is a significant need for bioassays useful to determine the activity of body fluid components, particularly enzymes such as proteases, on their respective target substrates. Although chromogenic or fluorogenic substrates have been used in the past to assay the activity of enzymes, there is a need for a method or assay which is rapid, efficient, inexpensive, and highly sensitive.

For example, an illustration of the usefulness of such assays is the measurement of components involved in fibrinogen polymerization, fibrinolysis, or fibrinogenolysis. Fibrinogen is the key structural protein in blood clot formation. It is a fibrous protein having three pairs of polypeptide chains held together by disulfide bonds. In fibrinogen polymerization, as illustrated in FIG. 1A, fibrinogen is a substrate for thrombin proteolytic activity. Thrombin catalyzes the release of small peptides, fibrinopeptides A and B, from the chains of fibrinogen. The removal of the fibrinopeptides from the fibrinogen substrate results in molecules which polymerize spontaneously into fibers in forming fibrin. After serving its role as the protein matrix of a blood clot, and in tissue repair, fibrin is then removed or degraded in the process of fibrinolysis.

As illustrated in FIG. 1B, the inactive precursor, plasminogen, is converted into the active proteolytic enzyme, plasmin. In fibrinolysis, plasmin catalyzes the fibrin substrate into soluble degradation products. Further, since plasmin is enzymatically active against fibrinogen, fibrinogenolysis is a process by which fibrinogen substrate is degraded into soluble products.

Measurement of the various enzymes, inhibitors, activators, and protein substrates involved in clot formation, inhibition of clot formation, or dissolution of clots (thrombolysis) has medical applications. For example, thrombosis is an important cause of human illness and death. Thrombolytic agents are increasingly used in pharmacological prevention and/or dissolution of formed thrombi such as in acute myocardial infarction.

Various methods for assaying various blood factors involved with the formation, inhibition, or degradation of clots have been described previously. Typically, these bioassays involve chromogenic assay techniques requiring enzyme labelling of the substrate, addition of the component(s) for which activity is to be measured, and subsequent detection of the amount of color formed. Similar bioassays have been described without the use of chromogens, but instead measure turbidity once the reaction has taken place. Disadvantages of these types of assays, particularly for the measurement of components which are normally in low concentrations in body fluid, include: susceptibility to diffusion artifacts; relative time consumption to perform the assay and obtain the results; the concentration of substrate that is required for the assay; lack of kinetic information of the process being measured; and lack of sensitivity of detection to the picomolar or nanomolar level. Thus, for applications such as monitoring thrombolytic agent therapy in a clinical setting, previously described methods have been found to be time-consuming and insufficiently sensitive.

Therefore, there is interest and need in providing assays which are rapid, highly sensitive, provide measurements of body fluid components which reliably reflect in vivo activity, and which can be used to detect and quantitate a wide variety of analytes including enzymes, enzyme inhibitors, and enzyme activators.

SUMMARY OF THE INVENTION

A novel method is provided for detecting and quantitating body fluid components involved in either enzyme-catalyzed protein polymer formation or enzyme-catalyzed protein polymer degradation. The method involves tagging a substrate with a fluorescent label. The substrate is the protein template with which molecular assembly with the respective enzyme occurs, and is also the molecule, in a modified form, that generates a signal that is directly detected since it has incorporated therein, molecules of fluorescent label. Depending on whether the enzymatic reaction involves polymerization or degradation, quenching or dequenching of the fluorescence emission is measured which relates directly to the kinetics and quantitation of modification of the substrate. Therefore, with a known amount of substrate, the activity of the respective enzyme is directly detected. The fluorescence emission also provides an indirect means for the quantitation of activity of an enzyme inhibitor or activator. The method avoids diffusion-limitation artifacts, and is useful for immediate (within minutes) determination of a component's activity.

DESCRIPTION OF THE SPECIFIC EMBODIMENTS

Figure 1A:
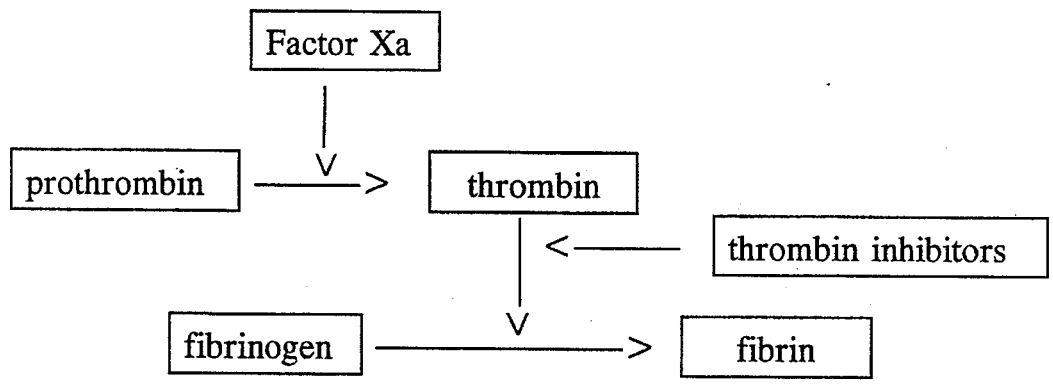
FIG. 1A is a schematic representation of fibrinogen polymerization.
Figure 1B:
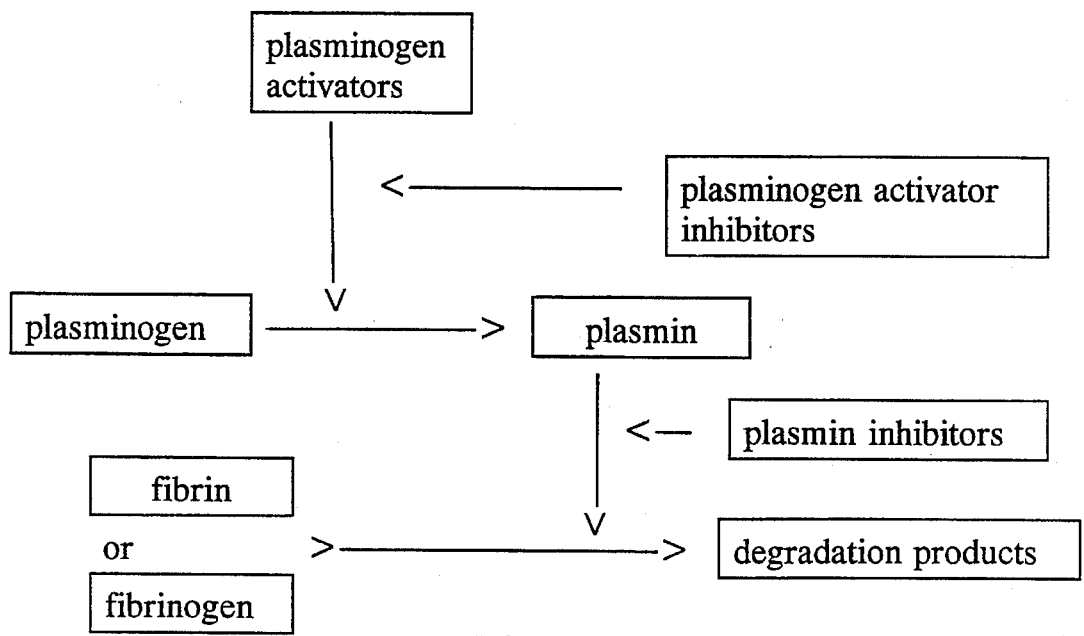
FIG. 1B is a schematic representation of fibrinolysis and fibrinogenolysis.

The method according to the invention for detecting and quantitating body fluid components involved in either enzyme-catalyzed protein polymer formation or enzyme-catalyzed protein polymer degradation is performed by using a substrate having been tagged with a fluorescent label. Because the substrate is the protein template with which molecular assembly with the respective enzyme occurs, and is also the molecule which in a modified form is directly detected since it has incorporated therein molecules of fluorescent label, enzymes that are dilute in solution achieve very high concentrations locally when assembled on the substrate. This gives the fluorescent-labeled substrate a very sensitive signal when used in low concentrations (e.g., 1 to 10 nM). This concentration is about 1000 fold lower than typical μM levels for fluorogenic or chromogenic substrates used in other assays that have no ability to concentrate molecules locally on a template.

In measuring components involved in a pathway which leads to polymerization of the substrate, the fluorescence of the label molecules of the polymerized substrate is quenched (reduced fluorescence emission), relative to the basal level of fluorescence prior to polymerization. The fluorescence quenching is due to enhanced neighbor-neighbor interactions between the fluorescent label molecules in the polymerized substrate. Measurement of quenching during the polymerization to an end point determination provides for information on the kinetics of the reaction. Measurement of fluorescence emission at the end point of quenching, relative to the basal level of fluorescence emission, can be used to quantitate enzyme activity, or enzyme activators or inhibitors, depending on the components included in the reaction mixture.

In measuring components involved in a pathway which leads to degradation or dissolution of the substrate or polymerized form of substrate, the fluorescence of the label molecules of the substrate or polymerized form of substrate is dequenched (increased fluorescence emission), relative to the basal level of fluorescence prior to degradation or dissolution. The fluorescence dequenching is due to an increase in the distance between neighboring molecules of fluorescent label as a result or unfolding or cleavage of the substrate or polymerized from of substrate; i.e., thereby being free from proximity-based quenching. Measurement of dequenching during degradation or dissolution to an end point determination provides for information on the kinetics of the reaction. Measurement of fluorescence emission at the end point of dequenching, relative to the basal level of fluorescence emission, can be used to quantitate enzyme activity, or enzyme activators or inhibitors, depending on the components included in the reaction mixture.

Body fluid components or components are terms used herein to refer to enzymes, enzyme inhibitors or enzyme activators found in body fluid which are involved in either a pathway of protein substrate polymerization, or a pathway of protein substrate dissolution or degradation. Enzyme inhibitors are proteins or factors which have activity that directly or indirectly inhibits or inactivates an enzyme. Although not found naturally occurring in body fluid, a pharmaceutical having enzyme inhibitor activity, for the purpose of the present invention, will also be included in the term "enzyme inhibitor". Enzyme activators are proteins or factors which interact with an enzyme in forming an active enzyme or active enzyme complex. Although not found naturally occurring in body fluid, a pharmaceutical having enzyme activator activity, for the purpose of the present invention, will also be included in the term "enzyme activators". Analytes are substances, including the protein substrate or other body fluid components that are detected and quantitated by the method of the present invention. "Measurement directly" is used herein to mean that the fluorescence emission changes reflect the direct effect an enzyme has on the substrate. "Measurement indirectly" is used herein to mean an inhibitive, competitive, enhancing secondary interaction on the direct effect between enzyme and substrate. "Basal level of fluorescence emission" is used herein to mean the fluorescence emission from a reference reaction. For example, when an enzyme's activity is being measured, the basal level of fluorescence would be that from a reaction containing the substrate and reaction mixture alone. When the activity of an enzyme inhibitor or enzyme activator is being measured, the basal level of fluorescence would be that from a reaction containing the substrate, enzyme, and reaction mixture.

Various protocols may be employed for the method according to the present invention depending upon the substrate used, and the different analytes to be measured. Similarly, different reagents may be necessary, and various components may need be added, depending upon the substrate used and analyte(s) to be measured. However, common to all embodiments of the method of the present invention is that the substrate in the method is a dimeric or oligomeric molecule, preferably naturally occurring as a body fluid component, which a) is labeled with fluorescent molecules; b) is modifiable in either an enzyme-catalyzed polymerization reaction or an enzyme-catalyzed degradation or dissolution reaction; c) where upon modification of the fluorescent-labeled substrate, a change in fluorescence emission results; and d) measurement of the difference between the fluorescence emission as a result of the reaction and the basal level of fluorescence emission (prior to substrate modification) directly relates to substrate concentration and/or enzyme activity and indirectly relates to the presence of absence of other components involved in that pathway. Thus, the substrate is a template with which molecular assemblies that occur in the body are recreated in the assay. The substrate being a dimer or oligomer facilitates the achievement of fluorescent labelling that is internally quenched.

Further common to all embodiments of the present invention, the various reagents or components of a reaction mixture are mixed in solution, and then incubated for a sufficient time to allow for a reaction to occur. Thus, in another aspect the method of the present invention differs from methods using chromogenic or fluorogenic substrates bound to a solid support, by obviating the need for a wash phase in which the solid phase is washed to remove unbound or non-specifically bound label. It is important to note that the method according to the present invention is capable of detecting, and measuring in both a kinetic (if desired) and endpoint fashion, the direct or indirect action of an unknown amount of analyte on the fluorescent-labeled substrate.

In one particular embodiment of the present invention, one or more components required in the processes of blood coagulation or blood fibrinolysis is the analyte. Since fibrinogen and/or fibrin are the key reactive species in these processes, and since there are multiple components that affect the processes, numerous embodiments of assays using fluorescent-labeled fibrin or fibrinogen may be performed according to the method of the present invention. Further, in addition to blood components being tested as analytes in the method according to the present invention, synthetic materials such as pharmaceuticals which may activate or inhibit a blood component involved in the processes of blood coagulation or blood fibrinolysis, may be the analyte.

In using either fibrin or fibrinogen as the substrate, depending on the analyte to be measured, the method of the present invention is an assay reflective of both binding and activity. For example, according to the method of the present invention, plasmin must bind the fluorescent substrate in order for a signal change from the basal level of fluorescence to occur; i.e., to initiate detection of plasmin enzyme activity. Thus, the assay of the present invention can detect either the activity of components (e.g. ε-amino caproic acid) which inhibit the binding of the enzyme (plasmin), or the activity of components that affect or inhibit the active site (e.g., $\alpha_2$-Antiplasmin) of the enzyme (plasmin). In contrast, assays in the art which contain a peptide of fibrin or fibrinogen as a substrate typically measure only components that affect plasmin activity, but not plasmin binding. Therefore the substrate used with the present invention is a natural or natural-like (e.g., recombinant) substrate which more accurately represents the particular pathway in body fluids compared to the smaller synthesized (e.g. peptide) substrates.

This embodiment of the assay is particularly useful for the detection and quantitation of fibrinolytic components with accuracy, rapidity, and sensitivity (nanomolar to picomolar range) not achievable in current commercially available assays. The accuracy, rapidity and sensitivity provided by the method of the present invention will particularly be appreciated in a clinical setting in which thrombolytic therapy is being monitored. Further, the assay of the present invention utilizes fluorescent labeling, and thus avoids the use radioactive labels and the attendant problems with their use. Therefore in a clinical setting, the assay may be carried out simply in a cuvette or a 96-well plate and then measured using a fluorimeter.

For example, when a enzyme that is active in clot formation or clot degradation is the analyte, it will be necessary to only include a substrate, such as fluorescent-labeled fibrinogen or fibrin depending on the enzyme, in a reaction mixture in solution such as diluted plasma. Thus, a blood sample would be taken; plasma from the blood sample would be isolated, diluted, and then added to plasma deficient in the enzyme to be tested but containing a known amount of fluorescent-labeled substrate. Thus, an enzyme-catalyzed reaction of the substrate is a measurable effect of the activity of the enzyme contained in the sample.

If an activator or inhibitor is the analyte, then components (i.e. precursors to the enzyme, and/or enzyme) other than the analyte required in that particular pathway may need be added if they are not already contained within the reaction mixture or plasma, in addition to the fluorescent-labeled substrate. The measurable effect would then relate to the activity of the analyte in the sample. Knowing the concentration of the enzyme and fluorescent-labeled substrate in a reaction will allow for indirect quantitation of the activity of an inhibitor or activator present in the sample.

The following examples are offered for the purposes of illustration, and not by way of limitation.

EXAMPLE 1

Various fluorescent molecules are known in the art which are suitable for use to label a protein substrate for the method of the present invention. Because substrates for the method of he present invention are dimeric or oligomeric molecules, incorporation of fluorescent label into more than one chain of the substrate will lead to quenching due to molecular proximity. A partial, but representative list of the class of such fluorescent molecules is illustrated as Table 1, and includes the respective excitation wavelength (EX) and emission wavelength (EM) for detection (in nanometers, "nm"). Common fluorescent labels for protein labeling include amine-reactive probes which are reactive to end terminal amines and the lysines of the protein substrate; isothiocyanates; succinimidyl esters; sulfonyl chlorides which are conjugated to the substrate through amine residues and tyrosine; sulfhydryl-reactive probes that react with thiols found in proteins; and the like. Depending on the fluorescent molecule used, methods of incorporating or tagging the substrate with the fluorescent molecule label include attachment by covalent or noncovalent means.

TABLE 1

| Fluorescent molecule | EX | EM |
| --- | --- | --- |
| Fluorescein isothiocyanate (FITC) | 491 nm | 515 nm |
| Tetramethylrhodamine isothiocyanate (TRITC) | 540 nm | 567 nm |
| carboxytetramethylrhodamine succinimidyl ester | 540 nm | 567 nm |
| carboxyfluorescein succinimidyl ester | 491 nm | 515 nm |
| TEXAS RED$^R$ sulfonyl chloride | 589 nm | 615 nm |
| 7-diethylamino-3-((4'iodoacetyl)amino)phenyl0-4-methylcoumarin | 382 nm | 472 nm |
| 5-iodoacetamidofluorescein | 491 nm | 515 nm |
| tetramethylrhodamine-5-(and 6)-iodoacetamide | 540 nm | 567 nm |
| N-(4,4-difluoro-5,7-dimethyl-4-bora-3a,4a-diaza-s-indacene-3-propionyl)-N'iodoacetyl-ethylenediamine | 504 nm | 510 nm |
| Coumarin malemide | 385 nm | 471 nm |
| Fluorescein malemide | 490 nm | 515 nm |
| Rhodamine malemide | 542 nm | 566 nm |

The protocol for labeling of substrate with fluorescent molecule may vary depending upon the fluorescent molecule used. Such protocols are known in the art for the respective fluorescent molecule. For example, a general protocol for labeling the protein substrate with FITC or TRITC is as follows. The protein substrate, such as fibrinogen, in a concentration from 0.1 to 10 mg/ml is dissolved in 0.1 to 0.2M bicarbonate buffer (pH 8.3 to 9). The substrate is then incubated with FITC or TRITC (1 mg/ml) with continuous stirring for 1 hour at 22° C. in a labeling buffer of 0.1M sodium bicarbonate (pH 9.0). The reaction is stopped with hydroxylamine (0.15M final concentration, freshly prepared), incubated for 1 hour, after which the labeled substrate is dialyzed extensively in the dark at 4° C., and then stored at −75° C. until used (since only nanomolar levels of substrate are required per reaction). Alternatively, to remove unincorporated fluorescent label from the labeled substrate, the substrate can be subjected to molecular sieve chromatography.

Generally, the protocol for labeling substrate with amine-reactive probes is the same as that of labelling with FITC or TRITC except that the fluorescent label (e.g. TEXAS RED® sulfonyl chloride) is incubated with the protein substrate for 1 hour at room temperature or 4° C. in 0.1 to 0.2M sodium bicarbonate solution at pH 8.3. The general protocol for labeling the substrate with a fluorescent molecule comprising a haloacetyl derivative (type of sulfhydryl-reactive label) is as follows. The protein substrate, such as fibrinogen, in a concentration of 0.1 to 10 mg/ml is incubated with iodoacetamide reagent at 0.1 to 10 mg/ml concentration for 1 hour at room temperature under neutral buffer conditions (pH <8.0) in the dark. The labeled protein can be separated from unincorporated label using molecular sieve chromatography or extensive dialysis in the dark. The resultant fluorescent-labeled substrate may then be stored frozen. For malemide derivatives (type of sulfhydryl-reactive label) the protein substrate, such as fibrinogen, in a concentration of 0.1 to 10 mg/ml is incubated with maleimide reagent at 0.1 to 10 mg/ml concentration for 1 hour at room temperature under neutral buffer conditions (pH<8.0) in the dark. The labeled protein can be separated from unincorporated label using molecular sieve chromatography or extensive dialysis in the dark.

EXAMPLE 2

There are some general considerations in practicing the method of the present invention. The assay reaction is performed in the liquid phase contained within a cuvette, the well of a microtiter plate, or like container suitable for fluorimetry. Typically, the inner surface of the container is preincubated with an inert protein, such as serum albumin, to substantially reduce or eliminate nonspecific binding of the fluorescent-labeled substrate to the surface. Alternatively, transparent, low protein-binding materials may be used as incubation wells.

The fluorescent-labeled substrate is diluted in a reaction buffer comprising a physiological saline solution. Likewise, if the sample to be analyzed requires dilution, the diluent should also comprise such a saline solution. A general saline buffer using HEPES, Tris, or phosphate buffer is suitable. Salt concentrations in the buffer can range from 0.1M to 0.5M salt such as NaCl. Thus, an exemplary buffer comprises 0.1M NaCl, 5 mM $CaCl_2$, and 10 to 50 mM Tris-HCl (pH 7.4). In general, a zinc salt (zinc ion, $Zn^{2+}$) should be avoided as it may precipitate out of solution a substrate such as fibrin. Buffer components should also be chosen to include those which do not inhibit polymerization or dissolution/degradation processes.

A fluorescence emission baseline is established before the sample containing the analyte is added to the reaction mixture. In that regard, the reaction should be performed to avoid the presence of any contaminating strongly fluorescent or quenching materials that overlap with the excitation or emission wavelength of the fluorescent-labeled substrate. Since the sample containing the analyte to be measured may be a body fluid, red blood cells may be present. The inclusion of hemoglobin or red blood cells in the reaction is not recommended, but may be tolerated in some conditions. The reaction buffer may also comprise platelet poor plasma into which the labeled-substrate is added.

The reaction is initiated by the addition of critical enzyme in the sample to the fluorescent substrate (e.g., thrombin to fibrinogen). The reaction mixture is then excited with light at a wavelength dependent on the fluorescent molecule used to label the substrate (see for example, Table 1). For example, using FITC-fibrinogen in the method according to the present invention, the optimal excitation is blue light (488 nm). Fluorescent emission is then measured with a light detector (i.e., photomultiplier tube) in a fluorimeter. For example, for FITC-labeled substrate, green emission light (515 nm) is collected using a photomultiplier tube inside a fluorimeter. The intensity of emission of fluorescent light is monitored continuously by sampling the emission at 0.5 to 10 times per second. The development of signal is dependent on the initial state of the fluorescent-labeled substrate and reaction events occurring on the substrate (resulting in either polymerization or degradation/dissolution). However, a range of typical reaction times to an end-point determination is 1 to 5 minutes. The assay may be carried out at temperatures ranging from about 4° C. to about 37° C., and preferably at room temperature or 37° C.

Other reagents (proteins, inhibitors, activators, etc.) can be added to the fluorescent-labeled substrate prior to start of the reaction. Alternately, it is possible to preincubate components of the reaction mixture together prior to addition of fluorescent-labeled substrate to the incubation mixture. For example, a preincubation reaction can include urokinase incubated with plasminogen to generate plasmin. In another embodiment, tPA (tissue plasminogen activator) can be incubated with unlabeled fibrin in the presence of plasminogen to generate plasmin. In either example, the preincubation reaction mixture can then be added to fluorescent-labeled fibrin or fluorescent-labeled fibrinogen substrate.

The use of a fluorescent-labeled substrate, as defined herein, to assay enzyme activities in a standard fluorimeter is novel. Because the substrate is a dimeric or oligomeric molecule, preferably naturally occurring as a body fluid component, and on which molecular assemblies that occur in the body are recreated, the molecular size of the substrate to be used in the method of the present invention is greater than about 100,000 daltons (e.g. the molecular size of fibrinogen is 340,000 daltons). Thus, the method of the present invention of following the fluorescence signal of such substrate during polymerization (with quenching of the signal) or proteolysis (with dequenching of the signal) is novel and very distinct from fluorescence polarization anisotropy measurements which are not useful for substrates having a molecular size above approximately 65,000 daltons.

Concerning assay reagents comprising components, other than the analyte, to be added to facilitate process of modification of the fluorescent-labeled substrate, in many instances it will not be necessary to use such components from the same species as the species of the analyte. For example, it is known that non-human components involved in fibrinolysis display cross-activity with the respective components found in humans. Thus, while the method of the present invention is preferably performed to measure analytes involved in human processes, assay reagents may include components from other species, if desirable. Further, various assay reagents useful for the particular process to be measured, can be included in a kit form to facilitate practice of the method of the present invention. In this regard, fluorescent-labeled substrate (e.g., FITC-fibrinogen) is stable for at least 9 months, and may be stable up to two years, with proper storage conditions.

EXAMPLE 3

Fibrinogen Polymerization

An assay for fibrinogen polymerization according to the method of the present invention was performed in accordance with materials and methods outlined in Examples 1 and 2. Fibrinogen was labeled with FITC using a 0.1M sodium bicarbonate buffer. After stopping the reaction with hydroxylamine (0.15M final concentration), the FITC-fibrinogen was dialyzed extensively before storage. The buffer for the polymerization reaction comprised either 0.1M NaCl, 0.05M Tris-HCl, 5 mM $CaCl_2$ ("buffer 1") or 0.3M NaCl, 0.05M Tris-HCl, 5 mM $CaCl_2$ ("buffer 2"). Cuvettes were incubated with 10 μM bovine serum albumin for 30 minutes to minimize adsorption of substrate to the cuvette walls.

In a series of reactions to produce fibrinogen polymerization into fibrin fibers, thrombin (final concentrations ranging from 0.1 U/ml, 0.25 U/ml, 0.5 U/ml and 1 U/ml) was mixed for about 5 seconds in either buffer 1 or buffer 2 containing a dilute FITC-fibrinogen (<40 nM) solution. Polymerization was monitored by exciting the reaction mixture with blue light (488 nm) and monitoring the fluorescence emission at 515 nm using a fluorimeter. The addition of thrombin to FITC-fibrinogen led to rapid and dose-dependent reduction of fluorescence emission due to quenching. At these extremely low concentration of fluorescent-labeled substrate (<40 nM), the solutions were optically clear and the drop in fluorescence was not due to turbidity or scattering effects during polymerization. Release of fibrinopeptides A and B from fibrinogen, mediated by thrombin action, caused no detectable dequenching of the FITC moieties on fibrin monomers.

Figure 2A:
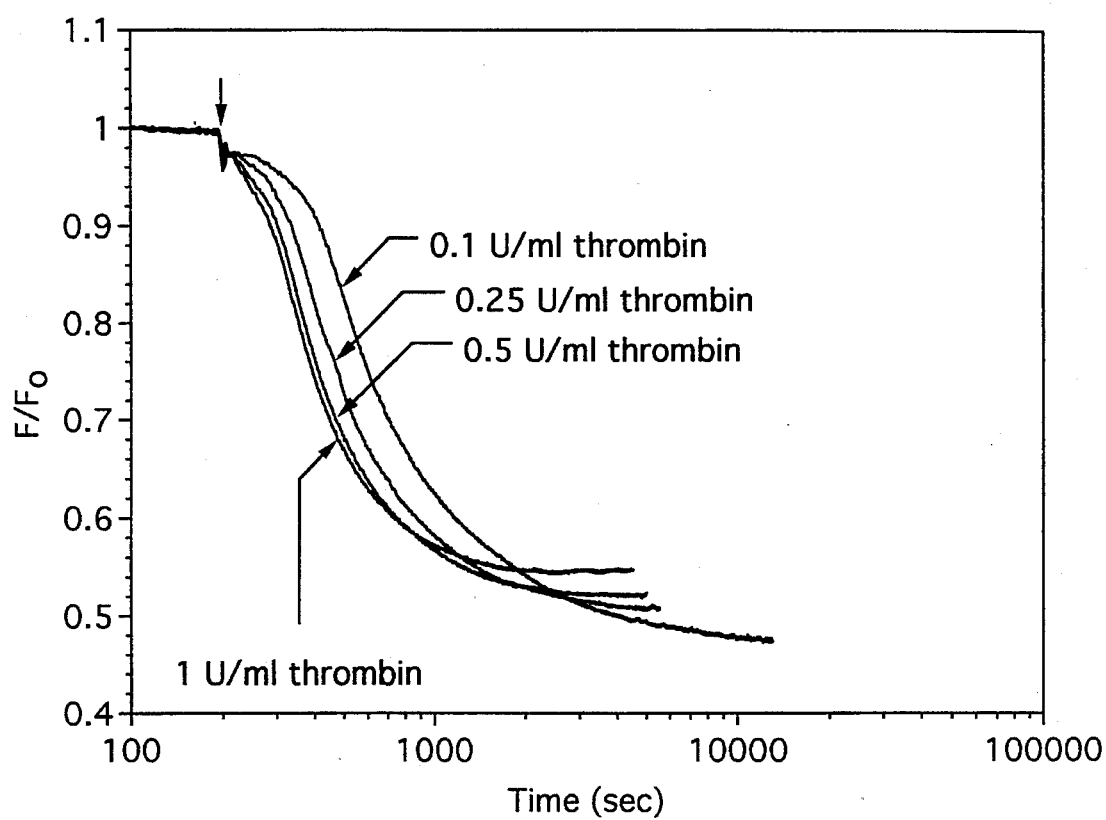
FIG. 2A is a graph illustrating dependence of fluorescence intensity of 30 nM fluorescent-labeled fibrinogen upon addition of 0.1 to 1.0 U/ml thrombin at 0.1M NaCl.
Figure 2B:
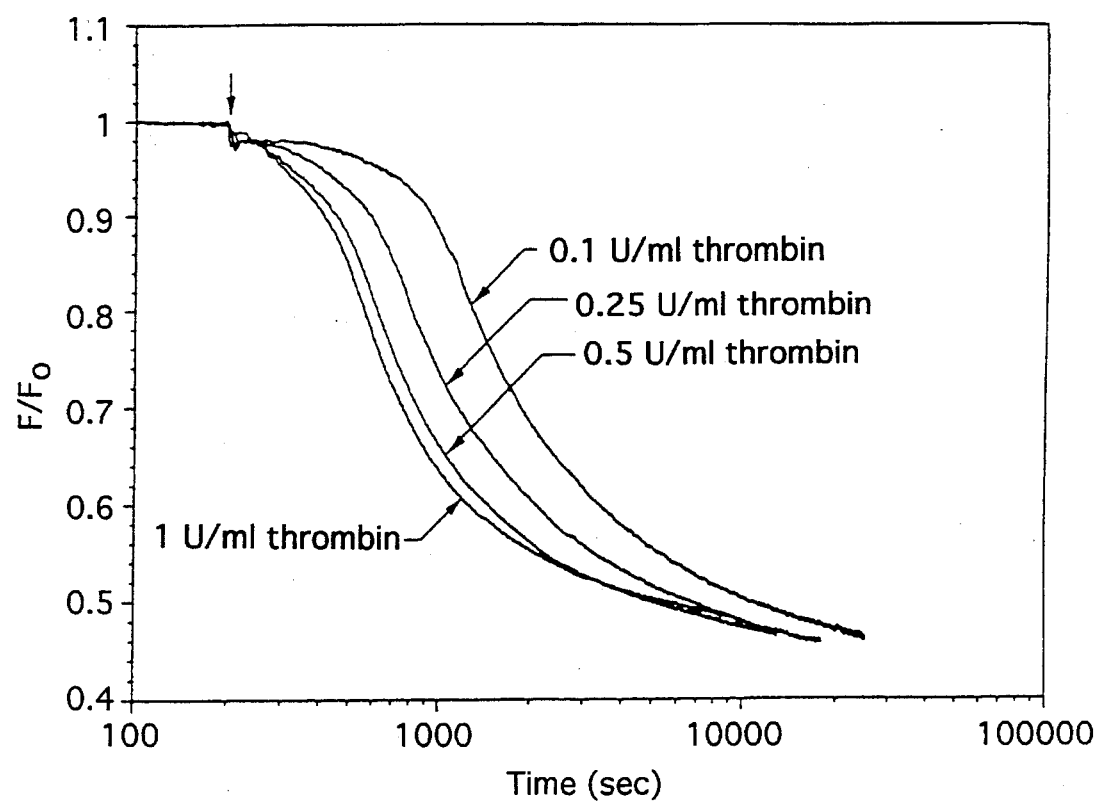
FIG. 2B is a graph illustrating dependence of fluorescence intensity of 30 nM fluorescent-labeled fibrinogen upon addition of 0.1 to 1.0 U/ml thrombin at 0.3M NaCl.

The initial rate of quenching was dependent on the initial concentration of thrombin, as illustrated in FIG. 2A (30 mM FITC-fibrinogen polymerized in buffer 1) and in FIG. 2B (30 mM FITC-fibrinogen polymerized in buffer 2). At the lowest concentrations of thrombin used, a comparatively significant lag time was observed before dequenching proceeded. After generation of sufficient monomer and protofibril extension, lateral aggregation of fibrils proceeded. Once dequenching began, the maximum rate of dequenching with time appeared to be largely independent of thrombin concentration, as seen by the similar maximum slopes on curves in FIGS. 2A or 2B. Also, the final extent of quenching appeared to be modulated by the thickness of the fiber. At low thrombin concentration and low salt (buffer 1) the thicker fibers that formed (taking longer to form) resulted in a greater final extent of quenching compared to the thinner fibers formed at higher thrombin concentrations (FIG. 2A). In high salt, favoring the formation of thinner fibers, the modulation of the final extent of quenching by adjusting the thrombin concentration was qualitatively similar to reactions with low salt, but the final differences were much smaller. As seen in FIGS. 2A and 2B, at all thrombin concentrations, the lag phase was considerably longer in buffer 2 as compared to in buffer 1, suggesting the importance of lateral aggregation during dequenching (i.e., protofibril extension is fast at higher salt concentrations). However, when quenching achieved its maximal rate at a given stage of the polymerization, there was little difference between that rate for low (buffer 1) and high (buffer 2) salt concentrations.

Figure 3A:
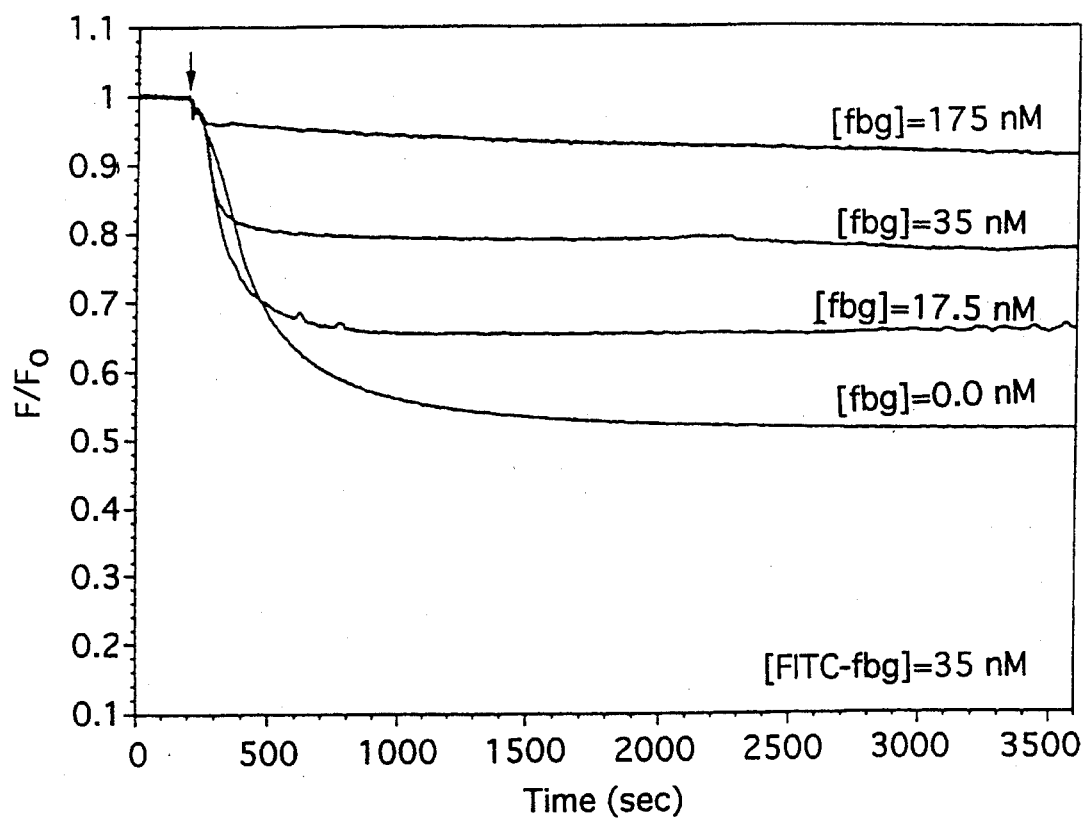
FIG. 3A is a graph showing the effects of addition of unlabeled fibrinogen to 35 nM of fluorescent-labeled fibrinogen prior to addition of 0.5 U/ml thrombin in 0.1M NaCl.
Figure 3B:
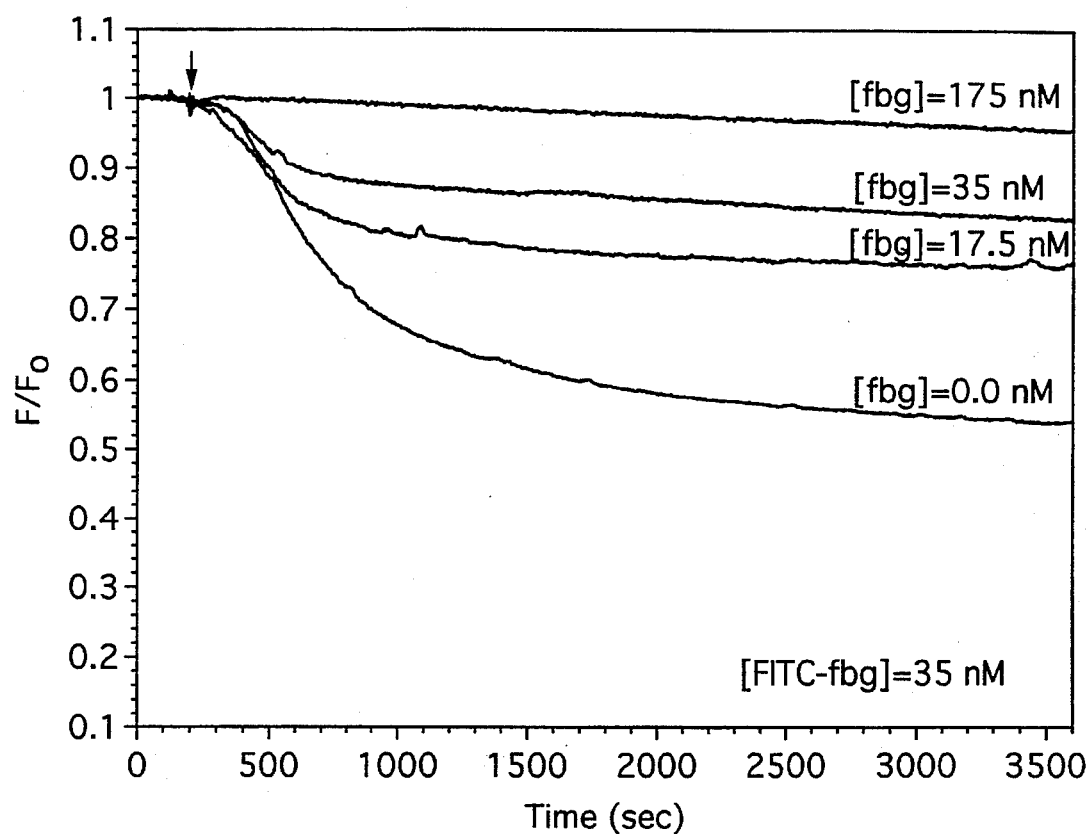
FIG. 3B is a graph showing the effects of addition of unlabeled fibrinogen to 35 nM of fluorescent-labeled fibrinogen prior to addition of 0.5 U/ml thrombin in 0.3M NaCl.

Addition of unlabeled fibrinogen to the reaction mixture attenuated the thrombin-induced quenching in a dose-dependent manner (FIGS. 3A and 3B). This result would not be seen for a scattering-based mechanism of loss of fluorescence signal. Increasing the concentration of unlabeled fibrinogen reduces the probability of two FITC-fibrin monomers either being incorporated sequentially in a protofibril or interacting within a given cross-section of fiber. Increasing the unlabeled fibrinogen in the reaction altered the initial quenching rate slightly (at constant thrombin concentration) and reduced the final extent of quenching in a dose-dependent manner. At a 5:1 ratio of unlabeled fibrinogen to FITC-fibrinogen, the quenching during polymerization was completely eliminated in fine fibers (FIG. 3A) while a small amount of quenching occurred at this ratio during polymerization of coarse fibers (FIG. 3B). This is consistent with an increased probability of two or more labeled FITC-fibrin monomers quenching each other in a thick fiber cross-section as compared to the quenching probability in a thin fiber-cross section which contains less fibrils. Thus, the quenching during polymerization is due to a mechanism involving molecular proximity which is achieved by two processes: fibril extension and fibril aggregation.

It was also observed that polymerization of FITC-fibrinogen by 1 U/ml of thrombin in the presence 0.1, 10, and 100 μM Gly-Pro-Arg-Pro ("GPRP", a peptide that prevents polymerization; Laudano et al., 1980 *Biochem.* 19:1013–1019) reduced in a dose-dependent manner the rate and extent of quenching associated with polymerization. Over 80% of the thrombin-induced quenching was prevented when 100 μM GPRP was added before polymerization. Similar to the findings given for unlabeled fibrinogen, this finding with GPRP verifies and validates the novel mechanism by which the assay works.

EXAMPLE 4

Thrombin Activity Assay

An assay for thrombin activity in fibrinogen polymerization according to the method of the present invention can be performed in accordance with materials and methods outlined in Examples 1, 2, and 3. The amount of biological sample, comprising body fluid to be tested for thrombin activity, to be added to the reaction mixture can range from about 1 μl to 100 μl, depending on the body fluid and if dilution of the sample is desirable. Likewise, one skilled in the art will appreciate that the amount of reaction buffer to which the sample is added (e.g., 0.1 ml to 2.5 ml) and the amount of FITC-fibrinogen in the reaction (e.g., 1 nM to 50 nM) will depend on the sample to be analyzed, and the mode (cuvette, microtiter well, etc.) in which the reaction takes place.

The sample is added to the reaction buffer containing FITC-fibrinogen. Polymerization is then monitored by exciting the reaction mixture with blue light (488 nm) and monitoring the fluorescence emission at 515 nm using a fluorimeter. In a parallel set of reactions, one or more thrombin standards (e.g., between 0.1 U/ml and 10 U/ml) may be used to calibrate the assay of the sample. The extent of quenching at the end of desired time interval (e.g., 5–25 minutes) is related to the thrombin activity, and hence the thrombin concentration, present in the sample. Since plasmin, if present in the sample, may cause fibrinogenolysis in an assay intended to measure thrombin activity in fibrinogen polymerization, a plasmin inhibitor may be added when measuring thrombin activity. For example, added to the reaction buffer containing the thrombin and FITC-fibrinogen may be a plasmin inhibitor, such as ε-amino caproic acid, to eliminate interference by plasmin contained in the sample.

If desired, the specificity of the reaction for thrombin activity may be validated by the addition of specific thrombin inhibitors, into the reaction mixture containing the sample and FITC-fibrinogen. Such thrombin inhibitors include natural inhibitors like antithrombin III, and synthetic inhibitors like benzamidine and D-phenylalanyl-L-prolyl-L-arginine chloromethyl ketone. Addition of a known amount of thrombin inhibitor will increase the amount of sample required (i.e., increase the amount of thrombin) to be added to obtain equivalent fluorescence emission. From the percent inhibition and from the thrombin concentration in the absence of inhibitor, can be calculated the increased thrombin activity (concentration) required to obtain equivalent activity.

EXAMPLE 5

Heparin Activity Assay (reverse thrombin assay)

Heparin and its variants are used in anticoagulation therapy, wherein it prevents fibrinogen polymerization by accelerating complexation of thrombin with antithrombin. An assay for heparin activity in fibrinogen polymerization according to the method of the present invention can be performed in accordance with materials and methods outlined in Examples 1, 2, 3, and 4.

The sample containing an unknown amount of heparin activity is added to the reaction buffer simultaneously with a known amount of thrombin (e.g., 1 U/ml), antithrombin (e.g., 0 to 5000 U/ml), and containing FITC-fibrinogen (e.g., 10 nM). Polymerization is then monitored by exciting the reaction mixture with blue light (488 nm) and monitoring the fluorescence emission at 515 nm using a fluorimeter. A parallel set of standard reactions containing thrombin, antithrombin, FITC-fibrinogen may be used to determine the maximum amount of fluorescence emission (quenching) during the desired time interval. The extent of interference of fibrinogen polymerization (i.e., inhibition of quenching) at the end of desired time interval in the reaction containing the sample, is related to the heparin activity, and hence the heparin concentration, present in the sample. Thus, from the percent inhibition of fibrinogen polymerization (as observed by a reduction in quenching) as compared to the standard(s), can be calculated the heparin activity (concentration) in the sample. Further, if desired, a parallel set of standard reactions may be performed containing thrombin, antithrombin, a known concentration of heparin, and FITC-fibrinogen for use to calculate the heparin activity (concentration) in the sample.

EXAMPLE 6

Antithrombin Activity Assay (reverse thrombin assay)

Antithrombin is a component that may be found in body fluid, wherein it prevents fibrinogen polymerization by direct suicide complexation with thrombin. An assay for antithrombin activity in fibrinogen polymerization according to the method of the present invention can be performed in accordance with materials and methods outlined in Examples 1, 2, 3, and 4.

The sample containing an unknown amount of antithrombin activity is added to the reaction buffer simultaneously with a known amount of thrombin (e.g., 1 U/ml), heparin (e.g., 0 to 5000 U/ml), and containing FITC-fibrinogen (e.g., 10 nM). Polymerization is then monitored by exciting the reaction mixture with blue light (488 nm) and monitoring the fluorescence emission at 515 nm using a fluorimeter. A parallel set of standard reactions containing thrombin, antithrombin, FITC-fibrinogen may be used to determine the maximum amount of fluorescence emission (quenching) during the desired time interval. The extent of interference of fibrinogen polymerization (i.e., inhibition of quenching) at the end of desired time interval in the reaction containing the sample, is related to the antithrombin activity, and hence the antithrombin concentration, present in the sample. Thus, from the percent inhibition of fibrinogen polymerization (as observed by a reduction in quenching) as compared to the standard(s), can be calculated the antithrombin activity (concentration) in the sample. Further, if desired, a parallel set of standard reactions may be performed containing thrombin, heparin, a known concentration of antithrombin, and FITC-fibrinogen for use to calculate the antithrombin activity (concentration) in the sample.

EXAMPLE 7

Fibrinogenolysis

An assay for fibrinogenolysis according to the method of the present invention was performed in accordance with materials and methods outlined in Examples 1 and 2. Fibrinogen was labeled with FITC using a 0.1M sodium bicarbonate buffer. After stopping the reaction with hydroxylamine (0.15M final concentration), the FITC-fibrinogen was dialyzed extensively before storage. The buffer for the lysis reaction comprised either 0.1M NaCl, 0.05M Tris-HCl, 5 mM $CaCl_2$ ("buffer 1") or 0.3M NaCl, 0.05M Tris-HCl, 5 mM $CaCl_2$ ("buffer 2"). Cuvettes were incubated with 10 μM bovine serum albumin for 30 minutes to minimize adsorption of substrate to the cuvette walls.

Figure 4:
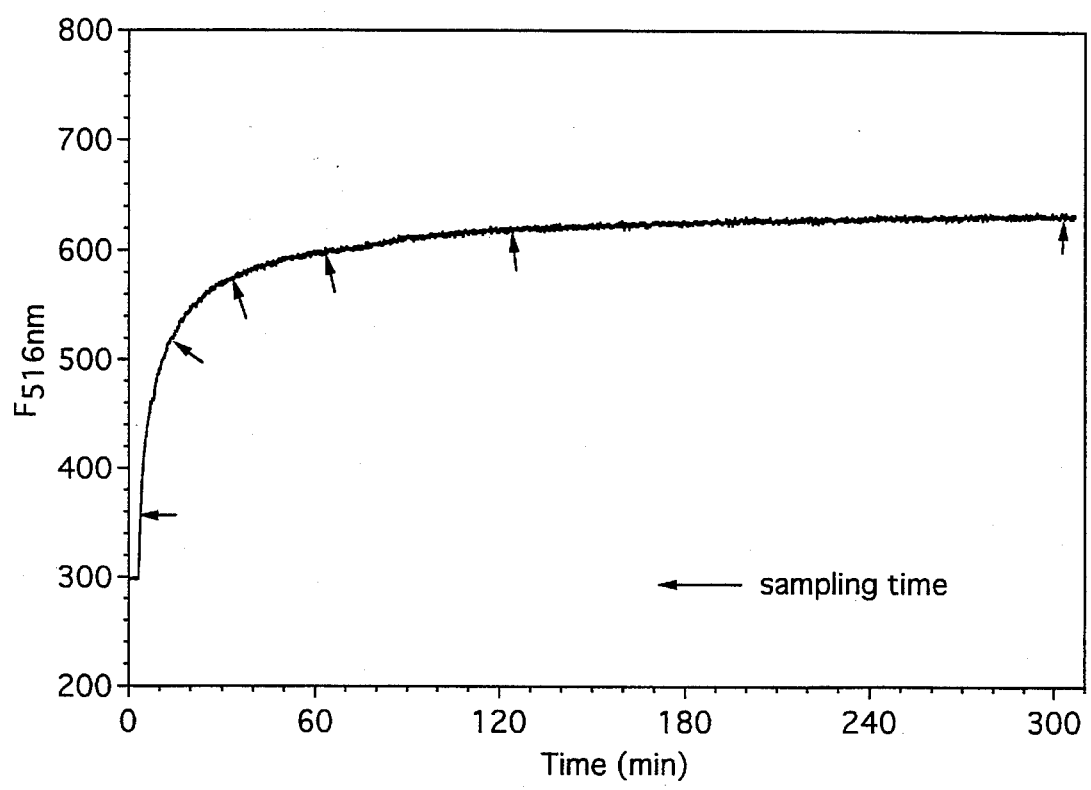
FIG. 4 is a graph showing fluorescence intensity of 250 nM fluorescent-labeled fibrinogen and 750 nM unlabeled fibrinogen upon addition of 10 nM plasmin.

To illustrate plasmin-mediated fibrinogenolysis into degradation products, 10 nM of plasmin was mixed for about 5 seconds in the reaction buffer containing 250 nM FITC-fibrinogen. Substrate degradation was monitored by exciting the reaction mixture with blue light (488 nm) and then simultaneously monitoring the fluorescence emission at 515 nm using a fluorimeter. The action of plasmin on FITC-fibrinogen produced an immediate large increase in fluorescence intensity (dequenching) in a plasmin-dependent manner (FIG. 4). The detection limit has been found under routine conditions to be at least 10 picomolar plasmin.

Degradation events were also monitored by sodium dodecyl sulfate polyacrylamide gel electrophoresis (SDS-PAGE), as indicated by the arrows representing sampling times (FIG. 4). Four fragments (X, Y, D and E) were detected in the degradation process. The major extent and most rapid rate of dequenching occurred at the earliest reaction times which correlated temporally with the degradation of fibrinogen to a fragment of about 200 kD (X) during the first three minutes of the reaction. A second fragment of about 140 kD (Y) first became visible by silver-stained SDS-PAGE after 3 minutes when over 50% of the dequenching had already occurred. Fragment Y reached its maximal concentration between 10 and 30 minutes after digestion was initiated when the dequenching rate had already slowed considerably. The obtainment of the final extent of dequenching was seen at 60 minutes and occurred concomitantly with the presence of the last remaining fragment X in the digestion. A third fragment (D) of about 85 kD appeared at about 10 minutes after digestion was initiated, and remained the prominent fragment from 30 to 300 minutes after the digestion was initiated. A fourth fragment (E) of about 45 kD appeared about 30 minutes after digestion was initiated, and again at 300 minutes, but not at 60 minutes and 120 minutes possibly due to its known, unreliable detection by silver staining.

During fibrinogenolysis, the total fluorescence emission at any time (F(t)) is related to the amount of emission from fluorescent-labeled fibrinogen ($\sigma[fbg(t)]$) and the amount of emission from individual fluorescent fibrinogen degradation products in the sample ($\Sigma\ \beta_i \cdot [FDP_i(t)]$). The intensity of fluorescence emission F(t) is described by Equation 1:

$$F(t)=\sigma[fbg(t)]+\Sigma\ \beta_i \cdot [FDP_i(t)]$$

where i= X, Y, D, E; and $\sigma=F(0)/[fbg(0)]$ at t=0

The majority of dequenching occurs temporally during the generation of fragment X. Thus, an initial reaction rate analysis would relate the rate of dequenching with the first reaction step- the rate of fragment X generation. All degradation products appear to have the same fluorescence intensity per molecule, $\beta$, which is justified by the fact that the dequenching signal reaches steady state long before lysis is complete; i.e., conversion of fragment Y to fragment D produced little additional dequenching. Plasmin degradation of one fibrinogen molecule can produce at least three dequenched fragments that include a single X fragment and at least two small fragments from the carboxy terminus of the $\alpha$ chains. For the reaction where plasmin converts one quenched fibrinogen molecule to n dequenched fragments (of different size, but the same $\beta$) with n$\geq$3, the Equation 1 becomes either:

Equation 2a $F(t)=\sigma[fbg(t)]+\beta \cdot [n$ dequenched fragment $(t)]$ or

Equation 2b $F(t)=\sigma[fbg(t)]+\beta' \cdot [X(t)]$ where $\beta'=\beta n$ and $\beta'=F_{max}/[fbg(0)]$ as all fibrinogen$\rightarrow$X Differentiating Eqn. 2(b) where $[fbg(0)]=[fbg(t)]+[X(t)]$, the rate of dequenching is related to X generation by Eqn. 3. One measure of the consistency of this approach is that the expression $[fbg(0)]/(F(0)-F_{max})$ which is equal to $1/(\sigma-\beta')$ was measured experimentally and found to remain constant as expected, regardless of reaction conditions.

Equation 3 $1/(\sigma-\beta')\ dF/dt=d[fbg]/dt=-d[X]/dt$

For kinetic analysis where reversible binding and dissociation occurred by distinct binding sites separate from the catalytic site, the rate of complex formation is described by:

Equation 4 $d[plm^b]/dt=k_f[plm^f]\ [\theta_{plm}-plm^b]-k_r[plm^b]$ (Diamond et al., 1993, *Biophysical J.* 65:2622–2643)

where the total available plasmin binding site concentration, $\theta_{plm}$, is equal to q·[fbg] and q=2 initially for two plasmin binding sites per fibrinogen molecule, $k_f$ is the forward association rate, and $k_r$ is the reverse dissociation rate (Lucas et al., 1983, *J. Biol. Chem.* 258:4249–4256).

At all times, the free plasmin concentration $[plm^f]$ plus the bound plasmin concentration $[plm^b]$ is equal to the initial plasmin concentration $[plm^o]$. For rapid binding that equilibrates quickly ($d[plm^b]/dt=0$), the concentration of bound plasmin is given by (Equation 5):

$$[plm^b]=\frac{(K_d+[plm^0]+q[fbg^0])-\sqrt{(K_d+[plm^0]+q[fbg^0])^2-4q[fbg^0][plm^0]}}{2}$$

and the initial reaction rate is given as:

Equation 6 $v=k_{cat} \cdot [plm^b]$

Figure 5:
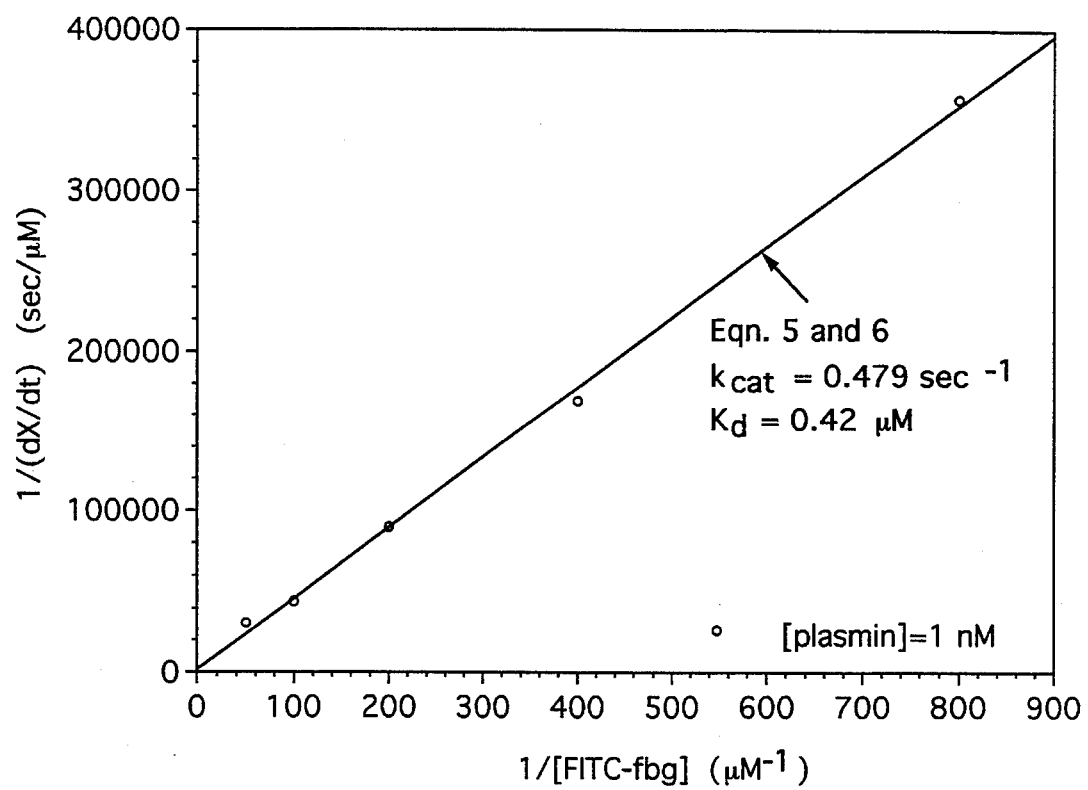
FIG. 5 is a graph represents a reciprocal plot showing the effect of fluorescent-labeled fibrinogen concentration (1.25 to 20 nM) on plasmin-mediated fibrinogenolysis. The theoretical curve using Equations 5 and 6 is shown for $k_{cat}=$ 0.479 sec$^{-1}$ and $K_d=0.42$ μM.

Using this model, as the initial concentration of fibrinogen increases to very large values (at constant plasmin concentration), the maximum rate goes to $v_{max}=k_{cat} \cdot [plm^o]$. As the initial plasmin concentration increases (at constant fibrinogen), the maximum reaction rate goes to $v_{max}=k_{cat} \cdot q[fbg^o]$. Using 1 nM plasmin and varying concentrations of fibrinogen from 1.25 to 20 nM in the method according to the present invention, a kinetic analysis for the generation of fragment X was conducted. A reciprocal plot is given for the initial rate of fragment X generation (FIG. 5) calculated from Equation 3. A linear regression of the experimental data allowed direct calculation of $v_{max}$ and a determination of $k_{cat}$=0.479 sec$^{-1}$. Using Equations 5 and 6, the $K_d$ (dissociation constant) of active plasmin binding to fibrinogen was then calculated to be 0.42 $\mu$M.

Figure 6:
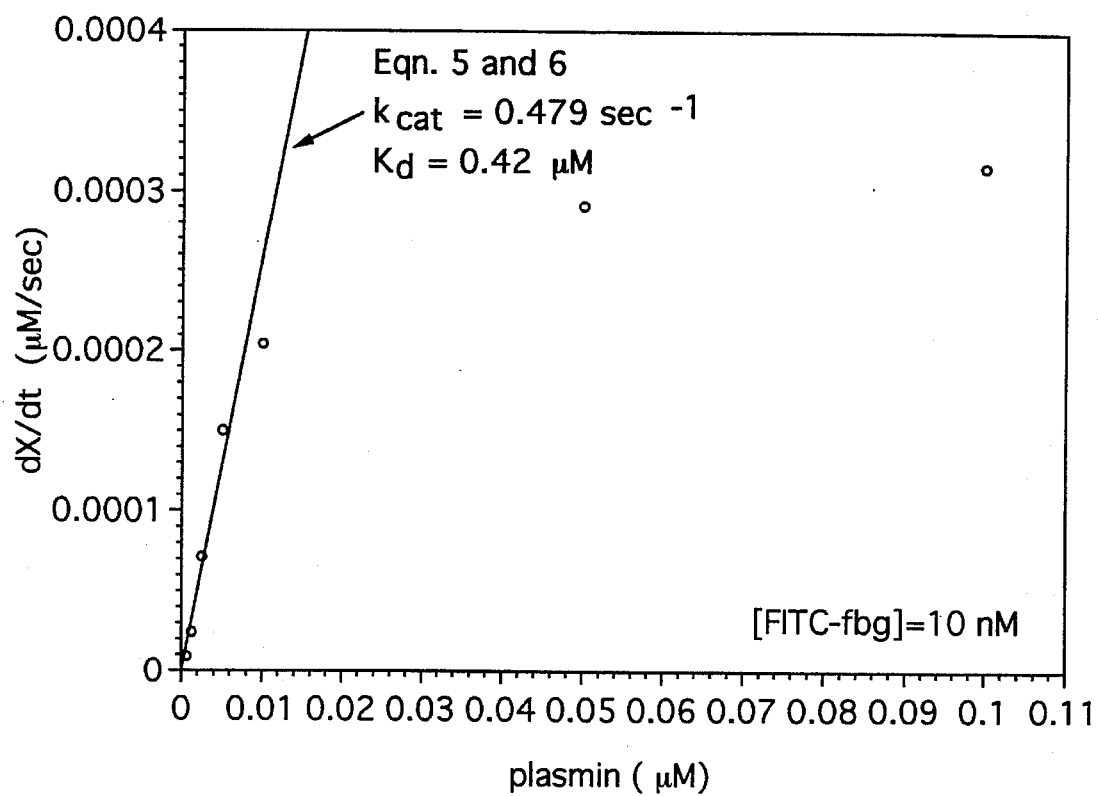
FIG. 6 is a graph showing the effect of increasing plasmin concentration on the initial rate of fragment X generation at constant concentration of fibrinogen (10.0 nM). The theoretical curve using Equations 5 and 6 is shown for $k_{cat}=$ 0.479 sec$^{-1}$ and $K_d=0.42$ μM.

Although enzyme assays are typically conducted under conditions of excess substrate, the sensitivity of the fluorescence-based method of the present invention allows determination of excess plasmin on nanomolar concentrations of fibrinogen. The fibrinogen substrate has two binding sites for plasmin, each with fairly high affinity for plasmin. Thus, it is expected that under the conditions of excess plasmin, these binding sites can be saturated with plasmin. This was indeed observed experimentally for the initial stage of the reaction when the ratio of plasmin to fibrinogen exceeded twice that of the initial concentration of fibrinogen (FIG. 6). Using values of $k_{cat}$=0.479 sec$^{-1}$ and $K_d$=0.42 $\mu$M, the kinetic rates for reactions where the plasmin/fibrinogen ratio was less than one were accurately predicted with Equations 5 and 6. A large deviation from the model was observed when the plasmin was in excess of the initial fibrinogen, a regime where kinetic formulations typically breakdown. Given the number of lysine binding sites per fibrinogen molecule, the measured reaction rates reached saturation at the expected plasmin concentrations, but the value of that maximum rate was considerably less than predicted. This may be due to the very short linear regime of the initial rate and the rapid destruction of fibrinogen such that the assumption of local binding equilibrium does not hold or the initial concentration of fibrinogen cannot be used in Equation 5 since it drops so rapidly at high plasmin concentration.

Figure 7:
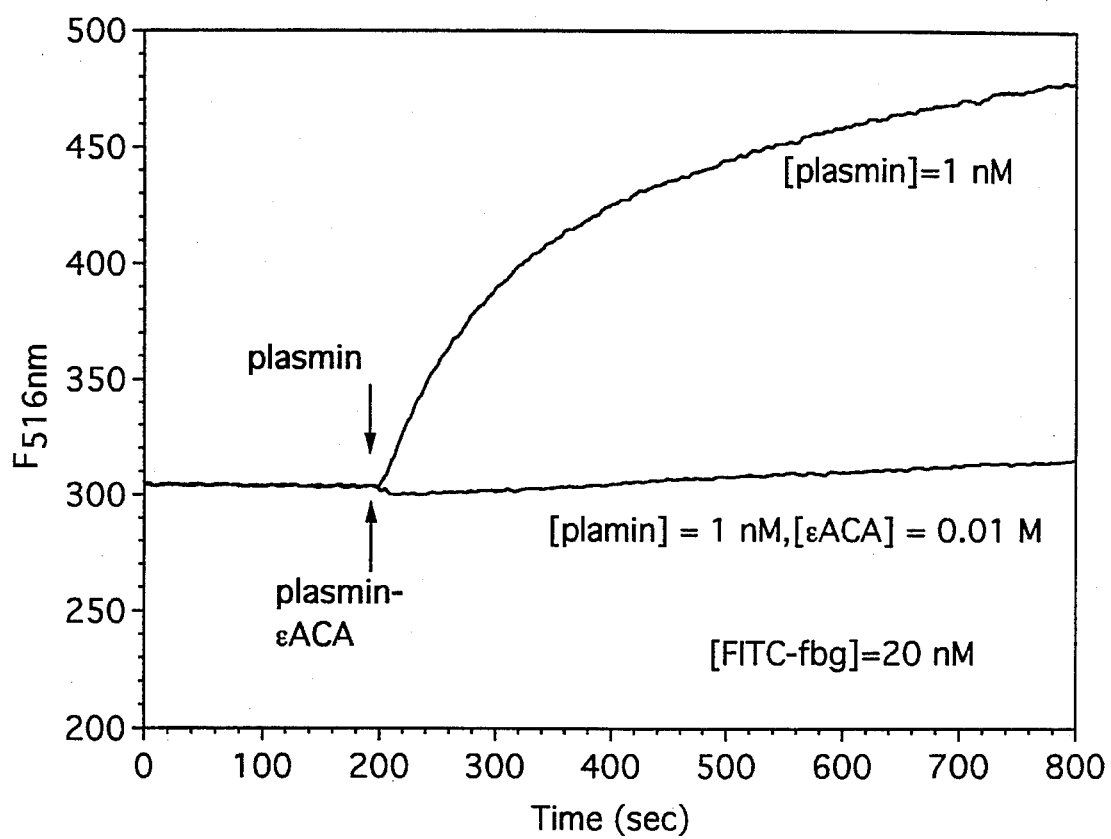
FIG. 7 is a graph showing the effect of dequenching by addition of ε-amino caproic acid-plasmin complex to fluorescent-labeled fibrinogen on dequenching compared to an equal amount of plasmin (1.0 nM) added to fluorescent-labeled fibrinogen.
Figure 8:
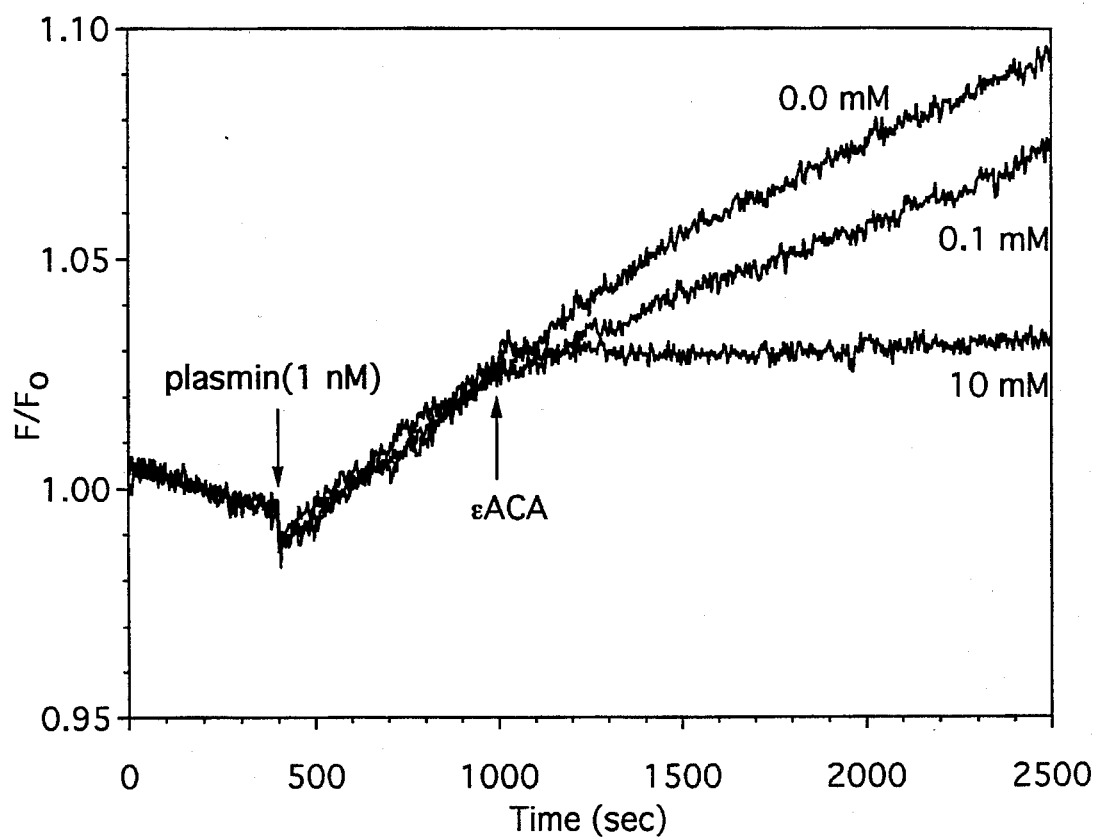
FIG. 8 is a graph showing the effect on dequenching by addition of ε-amino caproic acid (0.1 to 10 nM) to fluorescent-labeled fibrinogen (20 nM) undergoing degradation by plasmin (1.0 nM).

It was found that preincubation of plasin with $\epsilon$-amino caproic acid (10 mM) prior to addition of fluorescent-labeled fibrinogen greatly reduced the dequenching rate which indicates that plasmin must bind fibrinogen in order to initiate lysis (FIG. 7). Addition of excess $\epsilon$-amino caproic acid, after plasmin-mediated fibrinogenolysis was initiated, resulted in a dose-dependent inhibition of dequenching (FIG. 8). Addition of $\epsilon$-amino caproic acid (10 mM) immediately inhibited the progression of fibrinogenolysis as indicated by the cessation of dequenching. This indicated that plasmin can be removed from fibrinogen either by $\epsilon$-amino caproic acid disruption of fibrinogen-plasma complex or by $\epsilon$-amino caproic acid capture of desorbing plasmin. Addition of 10 nM plasmin to a mixture of 10 mM ε-amino caproic acid and 20 nM FITC-fibrinogen resulted in a competition between free plasmin binding with fibrinogen and plasmin binding with ε-amino caproic acid. In that competition, some plasmin was able to bind fibrinogen as indicated by the initial rate of dequenching.

EXAMPLE 8

Fibrinolysis

An assay for fibrinolysis according to the method of the present invention was performed in accordance with materials and methods outlined in Examples 1 and 2. To produce suspensions of fluorescent-labeled fibrin fibers, thrombin (final concentration of 1 U/ml) was mixed for 5 seconds with FITC-fibrinogen (80 nM) in either buffer 1 or buffer 2 after which the polymerization was monitored until fluorescence quenching was complete and stable for 1 hour. The daily-fiber suspensions yielded a highly repeatable extent of quenching and were stable for several hours as indicated by the stability of the fluorescence signal. Prior to reactions for fibrinolysis, cuvettes were incubated with 10 μM bovine serum albumin for 30 minutes to minimize adsorption of substrate to the cuvette walls. Small volumes of the FITC-fibrin were then pipetted into 2.4 ml of the reaction buffer and monitored for 200 to 400 seconds to establish the fluorescence baseline before addition of plasmin or other reagents.

Figure 9:
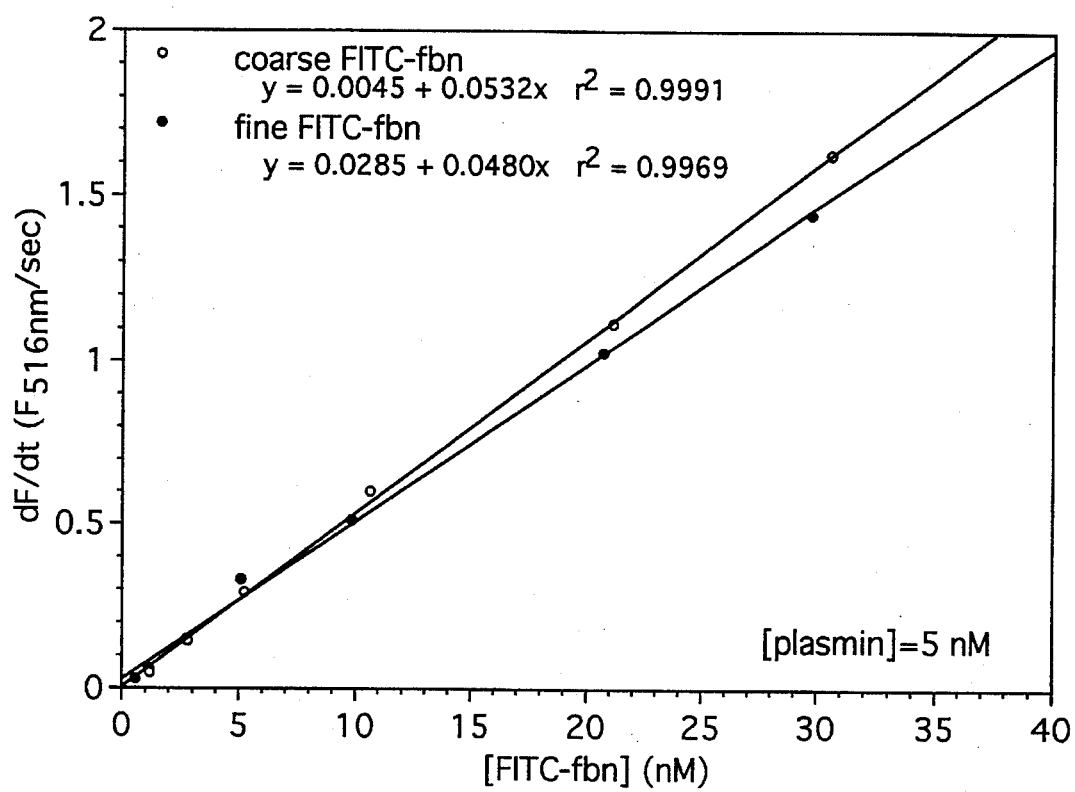
FIG. 9 is a graph showing the effect of fibrin concentration on the initial rate of dequenching by plasmin (5.0 nM) using coarse fibrin fibers (formed in 0.1M NaCl) or fine fibrin fibers (formed in 0.3M NaCl).

To illustrate plasmin-mediated fibrinolysis, plasmin (5 nM) was mixed for about 5 seconds in the reaction buffer containing between 0.5 to 30 nM FITC-fibrin. Polymerization was monitored by exciting the reaction mixture with blue light (488 nm) and monitoring the fluorescence emission at 515 nm using a fluorimeter. The action of plasmin on FITC-fibrinogen produced a large increase in fluorescence intensity (dequenching) in a plasmin-dependent manner. During fibrinolysis, the monomers in the fibrils are degraded with subsequent loss of fibril/fiber structure. The early dequenching during fibrinolysis is due to the loss of quenching in the fibril/fiber due to loss of structure, and the generation of dequenched degradation products. The initial rate of dequenching was very similar for lysis of coarse and fine fibers (FIG. 9) and was dependent on the concentration of fibrin used at constant plasmin concentration. It was noted that the final dequenched state of lysed fibrin (non-crosslinked) achieved a final fluorescence emission identical to the final dequenched state of lysed fibrinogen. Also, the initial rate of fluorescence change for FITC-fibrin in fibrinolysis appeared similar to that seen for FITC-fibrinogen in fibrinogenolysis.

EXAMPLE 9

Assays for Inhibitors of Fibrinolysis and Fibrinogenolysis

There are various plasmin inhibitors (also known as "antiplasmins") which may be present in body fluid and can inhibit fibrinolysis or fibrinogenolysis. Table 2 illustrates several of the physiologically important plasmin inhibitors.

TABLE 2

| plasmin inhibitor | Molecular size (kilodaltons, kD) | Approximate normal plasma/serum conc. |
|---|---|---|
| antiplasmin | 70 kD | 115–150 mg/dl$^{-1}$ |
| $\alpha_1$-antitrypsin | 51 kD | 100–160 mg/dl$^{-1}$ |
| $\alpha_2$-macroglobulin | 820 kD | 130–334 mg/dl$^{-1}$ |
| $C_1$ inhibitor | 90 kD | >11 mg/dl$^{-1}$ |
| inter-α-trypsin inhibitor | 170 kD | 20–70 mg/dl$^{-1}$ |
| antithrombin III | 62 kD | 200–400 mg/dl$^{-1}$ |

An assay for a plasmin inhibitor's activity in fibrinolysis or fibrinogenolysis according to the method of the present invention can be performed in accordance with materials and methods outlined in Examples 1, 2, 7, and 8.

The sample containing an unknown amount of plasmin inhibitor activity is added to the reaction buffer simultaneously with a known amount of plasmin (e.g., 5 nM) and FITC-fibrinogen or FITC-fibrin (e.g., 10 nM; "FITC-substrate"). Lysis of the FITC-substrate is then monitored by exciting the reaction mixture with blue light (488 nm) and monitoring the fluorescence emission at 515 nm using a fluorimeter. A parallel set of standard reactions containing a known amount of the plasmin inhibitor may be used to determine the amount of fluorescence emission (dequenching) during the desired time interval. The extent of interference of lysis of the FITC-substrate (i.e., prevention of dequenching) at the end of desired time interval in the reaction containing the sample, is related to the plasmin inhibitor activity, and hence the plasmin inhibitor concentration, present in the sample. Thus, from the percent inhibition of lysis of the FITC-substrate (as observed by a decrease in dequenching) as compared to the standard(s), can be calculated the plasmin inhibitor activity (concentration) in the sample. Further, if desired, a specific antithrombin agent can be added to prevent thrombin interference.

EXAMPLE 9

Assays for Plasminogen Activators

There are various plasminogen activators which may be present in body fluid and play an indirect role in fibrinolysis or fibrinogenolysis. Plasminogen is the inactive precursor of plasmin. Plasminogen activators are proteases that cleave plasminogen into plasmin. There are at least two biochemically distinct types: tissue-type (t-PA), approximately 70 kD in size, and urokinase-type or urinary (u-PA), approximately 33–53 kD. t-PA activating activity is enhanced by fibrin. Other substances, such as streptokinase produced by certain strains of streptococci, can function to activate plasminogen. Thus, the method of the present invention can be used to detect and measure plasminogen activator activity. Measuring plasminogen activator activity in body fluid is of clinical importance for several reasons. Plasminogen activators are used in therapeutic thrombolysis; i.e., therapy designed to degrade inappropriate fibrin deposition in blood vessels such as can occur in myocardial infarction. Also, some tumors have been shown to produce uPA, resulting in plasmin-mediated tumor-associated proteolysis that is related to the invasive and metastatic potential of malignant cells in a patient having such a tumor.

9.1 tPA Activity Assay

An assay for tPA activity in fibrinolysis or fibrinogenolysis according to the method of the present invention can be performed in accordance with materials and methods outlined in Examples 1, 2, 7, and 8.

A biological sample containing an unknown amount of tPA activity is added to the reaction buffer simultaneously with a known amount of plasminogen (e.g., 5 nM) and FITC-fibrin or FITC-fibrinogen (e.g., 10 nM; "FITC-substrate"). In this instance, it is noted that FITC-fibrin works better than FITC-fibrinogen because it contains tPA binding site that is not present prior to polymerization of fibrinogen. Lysis of the FITC-substrate is then monitored by exciting the reaction mixture with blue light (488 nm) and monitoring the fluorescence emission at 515 nm using a fluorimeter. A parallel set of standard reactions containing a known amount of tPA may be used to determine the amount of fluorescence emission (dequenching) during the desired time interval (i.e., in calibrating the assay). The extent of lysis of the FITC-substrate (i.e., dequenching) at the end of desired time interval in the reaction containing the sample, is related to the tPA activity, and hence the tPA concentration, present in the sample. Thus, the amount of lysis of the FITC-substrate (as observed by the amount of dequenching) as compared to the standard(s), can be calculated the tPA activity (concentration) in the sample. Further, if desired, to increase the sensitivity, tPA may be pre-incubated with plasminogen in the presence of unlabeled fibrin for a fixed period of time (e.g., 15 to 90 minutes) before addition of FITC-substrate. The detection limit is at least 20 picomolar tPA (single chain, recombinant) under routine conditions.

9.2 uPA Activity Assay

An assay for uPA activity in fibrinolysis or fibrinogenolysis according to the method of the present invention can be performed in accordance with materials and methods outlined in Examples 1, 2, 7, and 8.

A biological sample containing an unknown amount of uPA activity is added to the reaction buffer simultaneously with a known amount of plasminogen (e.g., 5 nM) and FITC-fibrin or FITC-fibrinogen (e.g., 10 nM; "FITC-substrate"). Lysis of the FITC-substrate is then monitored by exciting the reaction mixture with blue light (488 nm) and monitoring the fluorescence emission at 515 nm using a fluorimeter. A parallel set of standard reactions containing a known amount of uPA may be used to determine the amount of fluorescence emission (dequenching) during the desired time interval (i.e., in calibrating the assay). The extent of lysis of the FITC-substrate (i.e., dequenching) at the end of desired time interval in the reaction containing the sample, is related to the uPA activity, and hence the uPA concentration, present in the sample. Thus, the amount of lysis of the FITC-substrate (as observed by the amount of dequenching) as compared to the standard(s), can be calculated the uPA activity (concentration) in the sample. To increase the sensitivity, uPA may be preincubated with plasminogen in the presence of unlabeled fibrin for a fixed period of time (e.g., 15 to 90 minutes) before addition of FITC-substrate. The detection limit is at least 200 picomolar uPA under routine conditions.

EXAMPLE 10

In another embodiment, using the method of the present invention, and in accordance with materials and methods outlined in Examples 1–9, naturally-occurring molecular abnormalities fibrinogen ("dysfibrinogens") can be detected clinically. A sample suspected of containing a dysfibrinogen can be isolated from an individual. The apparent dysfibrinogen can be fluorescently labeled, and used as a fluorescent-labeled substrate in one or more of the assays measuring enzyme activity. For example, a dysfibrinogen has been described wherein there is a mutation in the thrombin-cleavage site (position 16 of the Aα chain) involved in fibrinogen polymerization to fibrin. Therefore, in an assay including the sample and a known amount of thrombin, interference with quenching as compared to a standard reaction containing a known amount of fibrinogen may be used to determine if the suspected dysfibrinogen is present in the sample.

EXAMPLE 11

While the preceding Examples disclose embodiments that illustrate the fluorescence-based method of the present invention in detecting and measuring activity of components involved or active in clot formation or dissolution, it will be apparent to those skilled in the art that the fluorescence-based method of the present invention can equally be applied to the detection and measurement of components active in other processes, provided that critical to such a process there is a protein substrate that is a template with which molecular assemblies that occur in the body are recreated. More particularly, the substrate is a dimeric or oligomeric molecule, preferably naturally occurring as a body fluid component, which a) can be labeled with fluorescent molecules; b) is modifiable in either an enzyme-catalyzed polymerization reaction or an enzyme-catalyzed degradation or dissolution reaction; c) where upon modification of the fluorescent-labeled substrate, a change in fluorescence emission results; and d) measurement of the difference between the fluorescence emission as a result of the reaction and the basal level of fluorescence emission (prior to substrate modification) directly relates to substrate concentration and/or enzyme activity and indirectly relates to the presence of absence of other components involved in that process.

In one embodiment, an assay for proteolytic activity of a sample containing an unknown amount of a proteolytic enzyme using the method of the present invention can be performed in accordance with materials and methods outlined in Examples 1, 2, 7, and 8. FITC-fibrin or FITC-fibrinogen can be used as a substrate to be degraded in detecting and measuring a sample containing an unknown amount of activity of a specific protease, including such proteases as trypsin, elastase, and papain. The extent of lysis of the FITC-substrate (i.e., dequenching) at the end of desired time interval in the reaction containing the sample, is related to the protease activity, and hence the protease concentration, present in the sample. Standard reactions containing a known amount of the protease may be run in parallel to calibrate the assay.

In another embodiment of the method of the present invention, and according to methods and materials outlined in Examples 1–9, a process or pathway other than clot formation or dissolution, and the components involved therein, can be detected and measured. For example, procollagen may serve as the substrate which is fluorescently labeled. Fluorescent-labeled procollagen is a substrate which can be added as a monomer or in a polymerized state in a reaction mixture along with a sample containing an unknown amount of activity of a component such as collagenase, gelatinase, and/or collagenase inhibitor to detect and measure the component in that sample using the method according to the present invention.

Although the present invention has been described in some detail by way of illustration and example for purposes of clarity and understanding, various modifications will become apparent to those skilled in the related arts from the foregoing description and figures. Such modifications are intended to be included within the spirit of this application and within the scope of the appended claims.

What is claimed is:

1. A method for measuring in a sample a body fluid component's activity in an enzyme-catalyzed polymerization reaction of a protein substrate, wherein the component is the enzyme that catalyzes the polymerization of said substrate, said method comprising the sequential steps of:

(a) measuring a basal level of fluorescence emission of a reaction mixture comprising a reaction buffer and a known amount of the substrate which has been labeled with fluorescent molecules, wherein the substrate
   (i) is selected from the group consisting of fibrinogen and procollagen,
   (ii) is soluble in the reaction mixture, and
   (iii) is a template on which molecular assemblies occur;

(b) contacting the sample with the reaction mixture;

(c) incubating the reaction mixture for a sufficient time for the polymerization reaction to occur in solution;

(d) exposing the reaction mixture to an excitation wavelength specific for the fluorescent molecules; and (e) detecting the fluorescence emission from the polymerization reaction wherein reduced fluorescence emission, relative to the basal level of fluorescence emission, is indicative of the polymerization of the fluorescent-labeled substrate and proportional to the enzyme's activity in the sample.

2. The method according to claim 1, wherein the sample is a body fluid selected from the group consisting of blood, serum, and plasma.

3. The method according to claim 1, wherein the enzyme-catalyzed polymerization reaction is fibrinogen polymerization into fibrin, wherein the substrate is fibrinogen, and wherein the enzyme activity to be measured in the sample is thrombin activity.

4. The method according to claim 1, wherein the fluorescent label is fluorescein isothiocyanate (FITC).

5. A method for measuring in a sample a body fluid component's activity in an enzyme-catalyzed polymerization reaction of a protein substrate, wherein the component is selected from the group consisting of an inhibitor and an activator of the enzyme that catalyzes the polymerization of said substrate, said method comprising the sequential steps of:

(a) measuring a basal level of fluorescence emission of a reaction mixture comprising a reaction buffer, a known amount of the substrate which has been labelled with fluorescent molecules, wherein the substrate
   (i) is selected from the group consisting of fibrinogen and procollagen and
   (ii) is soluble in the reaction mixture, and a known amount of the enzyme to catalyze the polymerization reaction if said enzyme is not present in the sample;

(b) contacting the sample with the reaction mixture;

(c) incubating the reaction for a sufficient time for the polymerization reaction to occur in solution;

(d) exposing the reaction mixture to an excitation wavelength specific for the fluorescent molecules; and (e) detecting the fluorescence emission from the polymerization reaction wherein reduced fluorescence emission, relative to the basal level of fluorescence emission, is indicative of the polymerization of the fluorescent-labeled substrate and proportional to the component's activity in the sample.

6. The method according to claim 5, wherein the sample is body fluid selected from the group consisting of blood, serum, and plasma.

7. The method according to claim 5, wherein the component is a pharmaceutical inhibitor of the enzyme.

8. The method according to claim 5, wherein the component is a pharmaceutical activator of the enzyme.

9. The method according to claim 5, wherein the component is an enzyme inhibitor selected from the group consisting of heparin and antithrombin, wherein the substrate is fluorescent-labeled fibrinogen, and wherein the enzyme is thrombin.

10. The method according to claim 9, wherein the fluorescent label is fluorescein isothiocyanate (FITC).

11. The method according to claim 5, wherein the fluorescent label is fluorescein isothiocyanate (FITC).

12. A method for measuring in a sample a body fluid component's activity in an enzyme-catalyzed degradation reaction of a protein substrate, wherein the component is the enzyme that catalyzes the degradation of said substrate, said method comprising the sequential steps of:

(a) measuring a basal level of fluorescence emission of a reaction mixture comprising a reaction buffer and a known amount of the substrate which has been labeled with fluorescent molecules, wherein the substrate
   (i) is selected from the group consisting of fibrinogen, fibrin, and collagen,
   (ii) is soluble in the reaction mixture, and
   (iii) is a template on which molecular assemblies occur;

(b) contacting the sample with the reaction mixture;

(c) incubating the reaction mixture for a sufficient time for the degradation reaction to occur in solution;

(d) exposing the reaction mixture to an excitation wavelength specific for the fluorescent molecules; and (e) detecting the fluorescence emission from the degradation reaction wherein increased fluorescence emission, relative to the basal level of fluorescence emission, is indicative of the degradation of the fluorescent-labeled substrate and proportional to the enzyme's activity in the sample.

13. The method according to claim 12, wherein the sample is a body fluid selected from the group consisting of blood, serum, and plasma.

14. The method according to claim 12, wherein the enzyme-catalyzed degradation reaction is a reaction selected from the group consisting of fibrinogenolysis and fibrinolysis and wherein the fluorescent-labeled substrate comprises fibrinogen when the enzyme-catalyzed degradation reaction is fibrinogenolysis and wherein the fluorescent-labeled substrate comprises fibrin when the enzyme-catalyzed degradation reaction is fibrinolysis, and wherein the enzyme activity to be measured in the sample is plasmin activity.

15. The method according to claim 12, wherein the fluorescent label is fluorescein isothiocyanate (FITC).

16. A method for measuring in a sample a body fluid component's activity in an enzyme-catalyzed degradation reaction of a protein substrate, wherein the component is selected from the group consisting of an inhibitor and an activator of the enzyme that catalyzes the degradation of said substrate, said method comprising the sequential steps of:

(a) measuring a basal level of fluorescence emission of a reaction mixture comprising a reaction buffer, a known amount of the substrate which has been labelled with fluorescent molecules, wherein the substrate
   (i) is selected from the group consisting of fibrinogen and procollagen and (ii) is soluble in the reaction mixture, and a known amount of the enzyme to catalyze the degradation reaction if said enzyme is not present in the sample;

(b) contacting the sample with the reaction mixture;

(c) incubating the reaction for a sufficient time for the degradation reaction to occur in solution;

(d) exposing the reaction mixture to an excitation wavelength specific for the fluorescent molecules; and (e) detecting the fluorescence emission from the degradation reaction wherein increased fluorescence emission, relative to the basal level of fluorescence emission, is indicative of the degradation of the fluorescent-labeled substrate and proportional to the component's activity in the sample.

17. The method according to claim 16, wherein the sample is body fluid selected from the group consisting of blood, serum, and plasma.

18. The method according to claim 16, wherein the component is a pharmaceutical inhibitor of the enzyme.

19. The method according to claim 16, wherein the component is a pharmaceutical activator of the enzyme.

20. The method according to claim 16, wherein the component is an inhibitor selected from the group consisting of antiplasmin, $\alpha_1$-antitrypsin, $\alpha_2$-macroglobulin, $C_1$ inhibitor, inter-$\alpha$-trypsin inhibitor, and antithrombin III; wherein the fluorescent-labeled substrate is fluorescent-labeled fibrinogen or fluorescent-labeled fibrin, and wherein the enzyme is plasmin.

21. The method according to claim 20, wherein the fluorescent label is fluorescein isothiocyanate (FITC).

22. The method according to claim 16, wherein the component is a plasminogen activator; wherein the fluorescent-labeled substrate is fluorescent-labeled fibrinogen or fluorescent-labeled fibrin, and wherein the enzyme is plasminogen.

23. The method according to claim 22, wherein the plasminogen activator is selected from the group consisting of tissue-type plasminogen activator (tPA) and urokinase-type plasminogen activator (uPA).

24. The method according to claim 22, wherein the fluorescent label is fluorescein isothiocyanate (FITC).

25. The method according to claim 16, wherein the fluorescent label is fluorescein isothiocyanate (FITC).

26. A method for determining the presence or amount of abnormal fibrinogen in a test sample, said method comprising the sequential steps of:

(a) obtaining said test sample from an individual suspected of having an abnormal fibrinogen;

(b) isolating the fibrinogen from said test sample;

(c) labelling said isolated fibrinogen with a fluorescent marker;

(d) diluting a known amount of said labelled isolated fibrinogen with a known amount of a buffer to form a test blank solution, such that the labelled isolated fibrinogen is soluble in the test blank solution;

(e) measuring the fluorescence of said test blank solution;

(f) adding a known amount of thrombin to said test blank solution and incubating for a sufficient time for thrombin-mediated polymerization of said labelled isolated fibrinogen to occur in order to form a test solution, such that the polymerized labelled isolated fibrinogen remains in soluble in the test solution;

(g) measuring the fluorescence of said test solution;

(h) measuring any fluorescence quenching caused by said polymerization by determining any decrease in fluorescence between steps (e) and (g);

(i) repeating steps (c) through (h) with a standard sample of known normal fibrinogen in lieu of the isolated fibrinogen from the test sample, before, after or simultaneously with the test sample; and (j) comparing the fluorescence quenching obtained from said test sample to the fluorescence quenching obtained from the standard sample to determine the presence or amount of said abnormal fibrinogen in said test sample, wherein said abnormal fibrinogen produces a proportionately lesser degree of quenching in said test sample relative to said standard sample.

* * * * *